(12) United States Patent
Heinz et al.

(10) Patent No.: US 6,960,195 B2
(45) Date of Patent: Nov. 1, 2005

(54) METERING RECEPTACLE

(76) Inventors: Jochen Heinz, Hauptstrasse 48, D-55578 Vendersheim (DE); Michael Spallek, Welfenstr. 14, D-55218 Ingelheim (DE)

( * ) Notice: Subject to any disclaimer, the term of this patent is extended or adjusted under 35 U.S.C. 154(b) by 39 days.

(21) Appl. No.: 09/918,405

(22) Filed: Jul. 30, 2001

(65) Prior Publication Data

US 2002/0013554 A1 Jan. 31, 2002

(30) Foreign Application Priority Data

Jul. 28, 2000 (DE) .......................................... 100 36 830

(51) Int. Cl.⁷ .............................................. A61M 5/315
(52) U.S. Cl. ....................... 604/222; 604/187; 604/218; 92/242; 92/243
(58) Field of Search .............................. 604/19, 27, 48, 604/93.01, 111, 118, 122–125, 131, 151, 152, 181, 184, 186, 187, 199, 207, 218, 220–222, 228, 230, 231; 92/172, 213, 240–243, 251, 259

(56) References Cited

U.S. PATENT DOCUMENTS

| | | | | |
|---|---|---|---|---|
| 2,761,447 A | * | 9/1956 | Hersee .......................... 604/89 |
| 3,161,195 A | * | 12/1964 | Taylor et al. .................. 604/89 |
| 3,958,570 A | * | 5/1976 | Vogelman et al. ........... 604/206 |
| 4,201,209 A | * | 5/1980 | LeVeen et al. ............... 604/218 |
| 4,576,917 A | * | 3/1986 | Schabron ..................... 436/85 |
| 4,613,326 A | * | 9/1986 | Szwarc ......................... 604/89 |
| 4,675,018 A | * | 6/1987 | Harden ......................... 604/407 |
| 4,776,704 A | * | 10/1988 | Kopunek et al. ........... 366/184 |
| 4,820,278 A | * | 4/1989 | Balisky ....................... 604/218 |
| 4,986,820 A | * | 1/1991 | Fischer ....................... 604/218 |
| 5,009,646 A | | 4/1991 | Sudo et al. |
| 5,163,919 A | * | 11/1992 | Thijs et al. .................. 604/199 |
| 5,273,542 A | * | 12/1993 | Blake, III ................... 604/110 |
| 5,607,400 A | * | 3/1997 | Thibault et al. ............. 604/230 |
| 5,743,889 A | * | 4/1998 | Sams .......................... 604/211 |
| 6,053,895 A | * | 4/2000 | Kolberg et al. ............. 604/218 |
| 6,296,893 B2 | | 10/2001 | Heinz et al. |
| 6,309,374 B1 | * | 10/2001 | Hecker et al. ............... 604/117 |
| 6,413,236 B1 | * | 7/2002 | Van Dyke .................... 604/110 |
| 6,482,187 B1 | * | 11/2002 | Gibbs .......................... 604/218 |

FOREIGN PATENT DOCUMENTS

WO      WO 88/09679      * 12/1988      .......... A61M/5/315

* cited by examiner

Primary Examiner—Anhtuan T. Nguyen
Assistant Examiner—Jennifer J Maynard
(74) Attorney, Agent, or Firm—Cohen, Pontani, Lieberman & Pavane

(57) ABSTRACT

A metering receptacle has an elongate hollow body which at one end has a closable exit opening, and which at the other end is closable by way of a plastic plunger stopper. The plunger stopper is at the same time longitudinally displaceable in the hollow body by way of a plunger rod. The metering receptacle is configured such that the plunger stopper is formed of two parts, with a sealing stopper part of plastic which is rigidly positionable in the elongate hollow body and has a centric bore for the passage of the plunger rod, and with a longitudinally displaceable plunger part of lubricious plastic which is connected to the plunger rod.

18 Claims, 2 Drawing Sheets

METERING RECEPTACLE

BACKGROUND OF THE INVENTION

The invention relates to a metering receptacle with an elongate hollow body which at one end comprises a closable exit opening and which at the other end is closable by way of a plastic plunger stopper which is accommodated in the hollow body in a longitudinally displaceable manner by way of a plunger rod.

Metering receptacles of this type are used in numerous application fields with a different specific design; for example for medical purposes (pharmaceutics and diagnostics) or for cosmetic applications as syringes with a syringe cylinder as a hollow body, or as plunger burettes in chemical analysis or as a dispenser.

Of particular importance with this are the prefilled disposable syringes, also called ready syringes or the prefilled disposable plunger burettes. Ready syringes of glass are for example known from DIN ISO 11040-4. Ready syringes of plastic are e.g. described in DE 44 38 360 A1. Prefilled disposable burettes are the subject-matter of DE 196 52 780.

With these prefilled ready syringes or plunger burettes it is necessary to incorporate a sliding layer onto the inside of the hollow body of the metering receptacle, in particular of the syringe body in order for the application to achieve sufficiently low friction forces on displacing the elastomer plunger. Only thus is a sufficiently fine-touch metering of the contents of the metering receptacle possible.

The incorporation of such sliding layers may be effected in various ways, as this is for example described in detail in DE 197 53 766.9 A1, which corresponds to U.S. Pat. No. 6,296,893. With glass syringes this is typically achieved by depositing and burning-in silicone emulsions at over 300°C., as is described in the article R. D. Anand, "Die Pharmazeutische Industrie" (The Pharmaceutical Industry) 54 No. 1, 1992, pages 69–73, "Spritzampullen: Em Vergleich in Zusammensetzung, Verarbeitung and Gebrauch vorgefuellter Spritzen" (Syringe ampullas: a comparison in composition, processing and use of prefilled syringes).

Sliding layers may likewise be deposited according to EP 0 202 915 B1 likewise with ionizing plasmas, wherein likewise silicon oil in the form of polydialkyl siloxane is used.

Furthermore, according to EP 0 338 671 B 1, which corresponds to U.S. Pat. No. 5,009,646, well sliding elastomer plungers may be manufactured when the elastomer plunger is coated with a special film material and has suitable dimensions. Although the use of special coating materials for elastomer plungers is a way of largely avoiding silicone as a lubricant, the manufacture of corresponding plunger stoppers is very expensive and significantly limits the geometric choice.

The use of sliding films based on silicon oil however has grave disadvantages, in particular with the use of the metering receptacle for medical purposes, in particular as a prefilled disposable syringe. Thus there may easily occur an interaction of the content substances, of the medicament with the silicon oil layer and with this essential active ingredients may be adsorbed by the silicon layer. Furthermore, a detaching of silicon oil droplets and/or flakes during the storage of the medicament may easily occur. Such problems are e.g. dicussed by V. Langlade and L. Caburet in "CURRENT ISSUES IN PACKAGING OF COMMON DILUENTS IN PREFILLED SYRINGES" PDA Fourth International Congress, Exhibition & Workshops Proceedings, page 153-page 165, 19–23 Feb. 1996.

Similarly with prefilled plunger burettes there may occur disadvantageous interactions between the contents of the burette and the silicone layer.

By way of DE 38 83 985 T 2 there is known a syringe for medical purposes which has good sliding properties of the plunger in the syringe body and requires no silicone sliding layer.

With the known syringe the elastomer plunger at the location at which it slides on the inner wall of the syringe cylinder has a fluroplastic plastic layer with a low dynamic friction coefficient and a thickness of approx. 5 m which is deposited by the method of low-temperature plasma polymerization.

Disregarding the expensive manufacture of such a plunger stopper, the known silicone-free syringe has the disadvantage that the coating material is very expensive and to a very limited degree is compatible to medication and capable of sterilization. Furthermore the micro-sealedness is not sufficiently given since the material comprises pores and is also not flexible enough, i.e. may not conform sufficiently sealingly on the inner wall of the syringe body.

SUMMARY OF THE INVENTION

The object of the present invention is to design the above described metering receptacle, with an elongate hollow body which at one end comprises a closable exit opening and which at the other end is closable by way of a plastic plunger part which is accommodated in the hollow body in a longitudinally displaceable by way of a plunger rod, such that a silicone sliding layer on the inner side of the elongate hollow body is not necessary without there being a restriction in the functioning by way of the plunger part or this having to be expensively manufactured.

The solution to this object is achieved according to the invention by providing a sealing stopper part of an elastomeric plastic which is fixed in its position in the elongate hollow body and comprises a centric bore for the passage of the plunger rod, and with a longitudinally displaceable plunger part of lubricious plastic which is connected to the plunger rod.

According to two alternative embodiments of the invention at the same time the plunger may be connected to the plunger rod as one piece or be releasably connected to this in particular by way of a screw connection. The last variant has advantages with regard the transport of the prefilled metering receptacle, since the elongate plunger rod need only be attached directly before the application of the receptacle contents.

For increasing the lubricity between the plunger rod and the stopper part in its centric bore in one embodiment of the invention on the outer circumference of the plunger rod there is provided a sliding layer, preferably a silicone layer. This sliding layer permits a fine-touch metering on application and by way of the sealing effect of the plunger part with respect to the inner wall of the elongate hollow body however no lubricant may get into the inside of the elongate hollow body. Alternatively to this, the metering receptacle may also be designed such that the plunger rod consists of a self-lubricating plastic, preferably PTFE.

With such a design the working step of depositing the sliding layer may be done away with.

The stopper part consists of a suitable elastomeric plastic. The sealing function given to it, microbiologically as well as mechanically (fluid-tight) is ensured in that the stopper part on its outer circumference as well as in the centric bore has peripheral sealing lips, preferably two or more sealing lips lying over one another.

In order to keep the lubricant securely away from the inner wall of the hollow body which lies in front of the plunger part and is in contact with the receptacle contents, and in order to support the sealing function of the plunger part in the storage condition of the prefilled metering receptacle, according to a further embodiment of the invention the plunger part on the side proximal to the stopper part comprises circumferential sealing lips.

In order to prevent on application, i.e. with the longitudinal displacement of the plunger part, the formation of a vacuum in the space between the plunger part and the fixedly positioned stopper part which is sealingly passed through by the plunger rod, on the plunger rod parallel to the axis there is formed a venting channel via which air may flow from the outside into the above mentioned space.

A preferred application of the invention is given when the metering receptacle is designed as a prefilled disposable receptacle, in particular as a ready syringe.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

There are shown in.

DETAILED DESCRIPTION OF THE INVENTION

Figure 1:
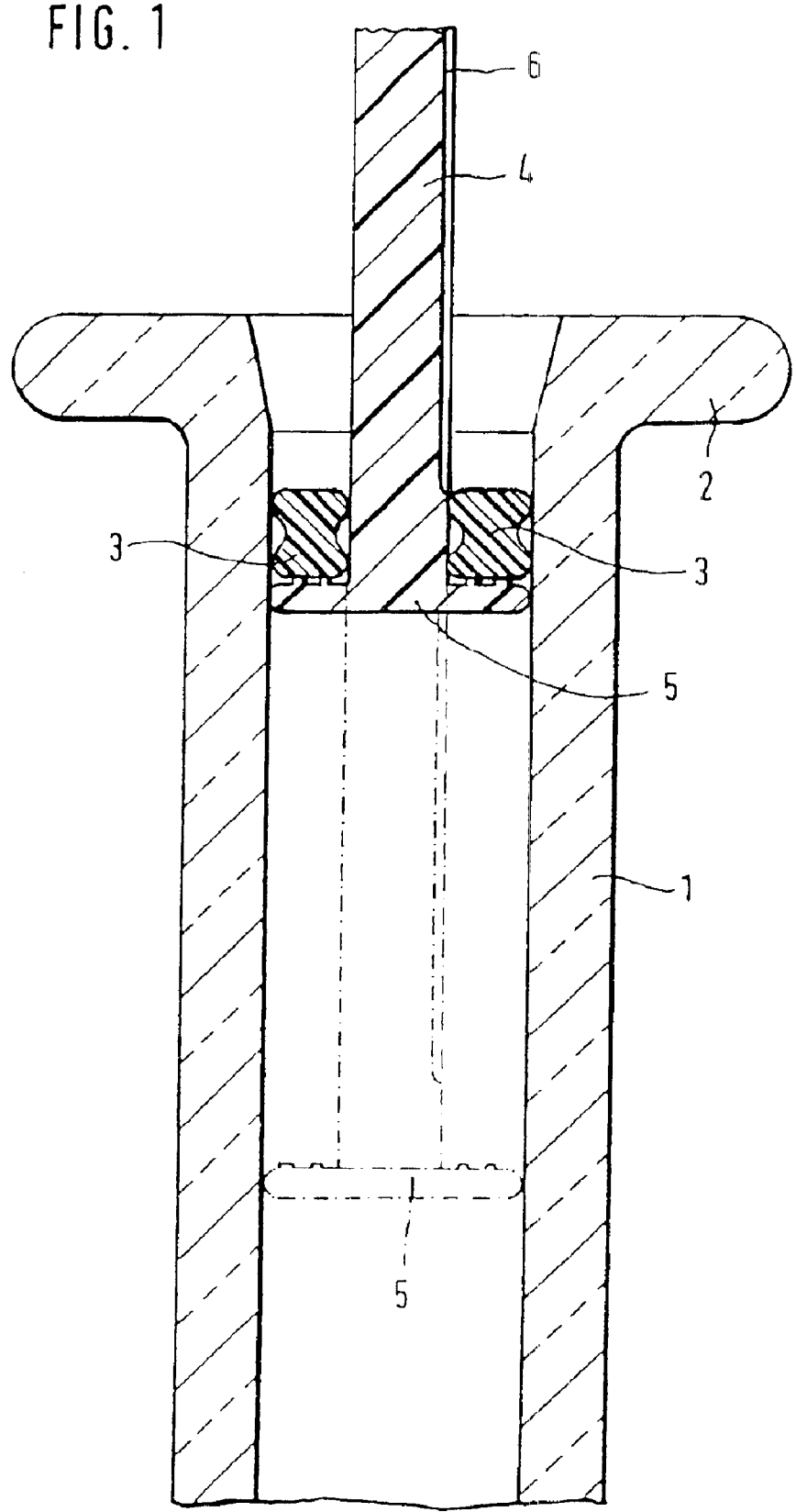
FIG. 1 in a longitudinal section, a cutout of a syringe for medical purposes with a special representation of the plunger stopper according to the invention on the end of the syringe body on the finger rest side.

FIG. 1 shows the rear part of a syringe cylinder 1 of a syringe for medical purposes, preferably a ready syringe, wherein the syringe cylinder 1 may alternatively consist of glass or plastic. At the end of the syringe cylinder 1 in the usual manner there is formed on a finger rest 2 which may also be a separate push part.

The end of the syringe cylinder 1 on the exit side, the syringe head, is designed in a conventional manner, i.e. runs either into a Luer lock closable by way of a tip cap or has an integrated injection needle, which may be covered by a needle cap of the usual type. Since this syringe-head side formation of the syringe is not significant for the invention, it is not illustrated.

With the invention it is the case of the design of the plunger stopper which on the one hand as a stopper must ensure the necessary sealing for the rearward closure of the syringe body and which on the other hand with the application procedure as a plunger must ensure the necessary transport of the contents of the syringe.

In contrast to the state of the art with a typical one-part elastomer plunger stopper which must achieve both functions, the plunger stopper is formed two-part.

The two-part plunger stopper according to the invention firstly comprises an elastomer stopper 3 which after placing in the syringe cylinder 1 remains fixed in its position at the rearward end of the syringe cylinder. By way of its usual peripheral labyrinth seals on the stopper outer side and in its bore accommodating a plunger rod 4 it ensures the mechanical, i.e. liquid and microbiological sealing with respect to the wall of the syringe cylinder and the plunger rod during the storage of the syringe, i.e. it ensures the stopper function.

Figure 2:
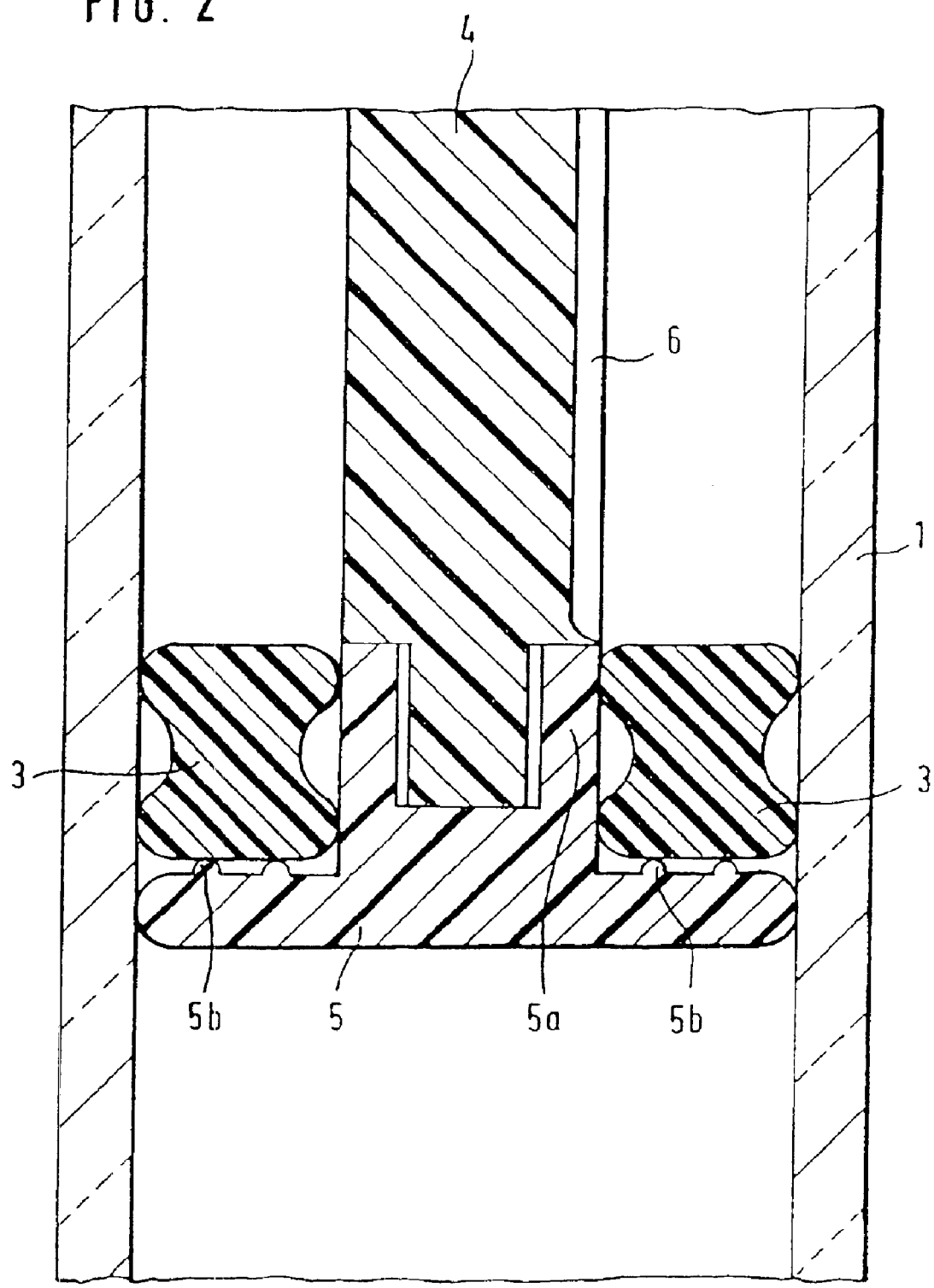
FIG. 2 an enlarged cutout of the longitudinal representation according to FIG. 1, which shows the stopper according to the invention in more detail.

The two-part plunger stopper according to the invention further comprises a circular-disk-shaped plunger part 5 which, as shown in FIG. 1, may be connected to the plunger rod 4 as one piece or which, as shown in FIG. 2, has a connection piece 5a for the usual releasable accommodation of the plunger rod 4.

This plunger part 5 consists of a plastic with a high sliding property (i.e., is lubricous) and a high medicament-compatibility with sealing lips 5b towards the fixed position elastomer stopper 3. This plunger part 5 is therefore the movable part of the plunger stopper according to the invention which is in contact with the medicament and on application ensures the transport of the contents of the syringe. At the same time it ensures the necessary mechanical sealing during the application and supports the microbiological sealing during the storage of the syringe, i.e. it ensures the plunger function.

On application, as is shown dashed in FIG. 1, only the plunger part 5 is advanced in the direction of the syringe head. So that a fine-touch application is possible, on the circumference of the plunger rod 4 there is deposited a sliding layer, preferably a silicon lubricant layer with usual methods. On account of the effect of the plunger part 5 which in as much is also sealing, this silicon lubricant layer in no phase of the storage or application is in contact with the medicament so that a silicon-free application is given.

In place of a lubricative silicone layer attached on the plunger rod, this plunger rod 4 may also consist of self-lubricating material, e.g. PTFE.

So that with the application, behind the plunger part there does not remain a vacuum, on the plunger rod there is formed a venting channel 6 via which the air may flow from the outside.

- during the storage and the application it is microbiologically and mechanically sealed,
- on account of the equalized adhesive and lubricative friction only very small application forces are necessary which permits a fine-touch metering of the contents of the syringe,
- due to the plunger stopper there is no impairment of the contents of the syringe, and
- no lubricant, in particular no silicon oil is in contact with the contents of the syringe.

If then the ready syringe for medical applications represents a very preferred application of the invention, also the application in other fields of use mentioned initially is possible, where comparable advantages are given.

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

We claim:

1. A metering receptacle, comprising:
    an elongate hollow body having a first end with a closable exit opening and a second end;
    a plunger part of lubricious plastic accommodated in the hollow body in a longitudinally displaceable manner so as to contact the hollow body at all positions of the plunger part in the hollow body;
    a plunger rod attached to the plunger part; and
    a sealing stopper part of plastic which occupies a fixed position completely within the elongate hollow body and has a centric through-bore for the passage of the plunger rod, wherein the stopper part is a one piece stopper part which sealingly contacts the hollow body and sealingly contacts the plunger rod when the plunger part is against the stopper part;
    wherein the displaceable plunger part is movable away from the sealing stopper part when the plunger rod is moved through the through-bore, said plunger part having circumferential sealing lips on a side facing said stopper part.

2. A metering receptacle according to claim 1, wherein the plunger part is formed as one piece with the plunger rod.

3. A metering receptacle according to claim 1, wherein the plunger part is releasably connected to the plunger rod.

4. A metering receptacle according to claim 3, wherein the plunger part is connected to the plunger rod by a screw connection.

5. A metering receptacle according to claim 1, wherein a sliding layer is deposited on an outer circumference of the plunger rod.

6. A metering receptacle according to claim 5, wherein the sliding layer is a silicone layer.

7. A metering receptacle according to claim 1, wherein the plunger rod is made of a self lubricating plastic.

8. A metering receptacle according to claim 7, wherein the rod is made of PTFE.

9. A metering receptacle according to claim 1, wherein the stopper part is of an elastomer plastic.

10. A metering receptacle according to claim 1, wherein the stopper part has peripheral sealing lips on its outer circumference as well as in the centric bore.

11. A metering receptacle according to claim 10, wherein the stopper part has at least two sealing lips lying over one another on at least one of said outer circumference and said centric bore.

12. A metering receptacle according to claim 1, wherein the plunger rod has a venting channel parallel to a longitudinal axis of the plunger rod.

13. A metering receptacle according to claim 1, wherein the metering receptacle is a prefilled disposable receptacle.

14. A metering receptacle according to claim 13, wherein the receptacle is a ready syringe.

15. A metering receptacle comprising:
    an elongate hollow body having a first end with a closable exit opening, an opposed second end, and a passage of uniform cross-section between said ends;
    an elastomeric sealing stopper part which occupies a fixed position in the passage toward the second end, said stopper part having a centric through-bore;
    a plunger part of lubricious plastic located in said passage and displaceable away from said sealing stopper part, said plunger part and said sealing stopper part completely sealing said second end of said hollow body when said plunger part is located against said sealing stopper part, said plunger part having circumferential sealing lips on a side facing said stopper part, said lips pressing into said elastomeric stopper part to provide a seal when said plunger part is located against said stopper part; and
    a plunger rod attached to the plunger part and received through said through-bore of said sealing stopper part.

16. A metering receptacle as in claim 15 wherein said plunger part and said plunger rod are formed as one piece.

17. A metering receptacle as in claim 15 wherein said sealing stopper part is made as a single piece which sealingly engages said hollow body and sealingly engages said plunger rod when said plunger part is located against said sealing stopper part.

18. A metering receptacle as in claim 17 wherein said plunger rod comprises a venting channel which communicates with said passage when said plunger part is displaced away from said sealing stopper part.

* * * * *